United States Patent [19]
Ganem

[11] Patent Number: 6,022,350
[45] Date of Patent: Feb. 8, 2000

[54] BONE FIXING DEVICE, IN PARTICULAR FOR FIXING TO THE SACRUM DURING OSTEOSYNTHESIS OF THE BACKBONE

[75] Inventor: Franck Ganem, Caen, France

[73] Assignee: Stryker France S.A., France

[21] Appl. No.: 08/854,412

[22] Filed: May 12, 1997

[30] Foreign Application Priority Data

May 13, 1996 [FR] France ................................ 96 05898

[51] Int. Cl.⁷ .................................................. A61B 17/70
[52] U.S. Cl. ................................ 606/61; 606/69; 606/73
[58] Field of Search .............................. 606/69, 70, 71, 606/61, 60, 72, 73

[56] References Cited

U.S. PATENT DOCUMENTS

| | | | |
|---|---|---|---|
| 4,696,290 | 9/1987 | Steffee ........................................ | 606/69 |
| 5,324,290 | 6/1994 | Zdeblick et al. ........................... | 606/61 |
| 5,443,467 | 8/1995 | Biedermann et al. ..................... | 606/72 |
| 5,520,690 | 5/1996 | Errico et al. ............................... | 606/61 |
| 5,531,746 | 7/1996 | Errico et al. ............................... | 606/61 |
| 5,607,426 | 3/1997 | Ralph et al. ............................... | 606/61 |
| 5,669,911 | 9/1997 | Errico et al. ............................... | 606/61 |

FOREIGN PATENT DOCUMENTS

| | | |
|---|---|---|
| 0201024 | 4/1986 | European Pat. Off. . |
| 0625337 | 5/1994 | European Pat. Off. . |
| 0654249 | 11/1994 | European Pat. Off. . |

*Primary Examiner*—Michael Buiz
*Assistant Examiner*—David O. Reip
*Attorney, Agent, or Firm*—Blakely Sokoloff Taylor & Zafman

[57] ABSTRACT

A bone fixing device, in particular for fixing to the sacrum for osteosynthesis of the backbone, comprises elongate link means receiving at least one bone-fastening screw, which passes through an orifice formed in the link means. In the bottom of the link means there is included a bearing surface of essentially circular cross-section. The head of the screw includes an essentially spherical surface for bearing against said bearing surface. The link means include a first thread in the vicinity of said orifice. The device further includes a plug having a second thread suitable for co-operating with the first thread, the plug being suitable for coming into clamping contact against said screw head to hold it in a desired angular position. According to the invention, the link means are constituted by a single-piece plate-shaped element having the orifice and the first thread formed therein, and said bearing surface is essentially spherical.

20 Claims, 6 Drawing Sheets

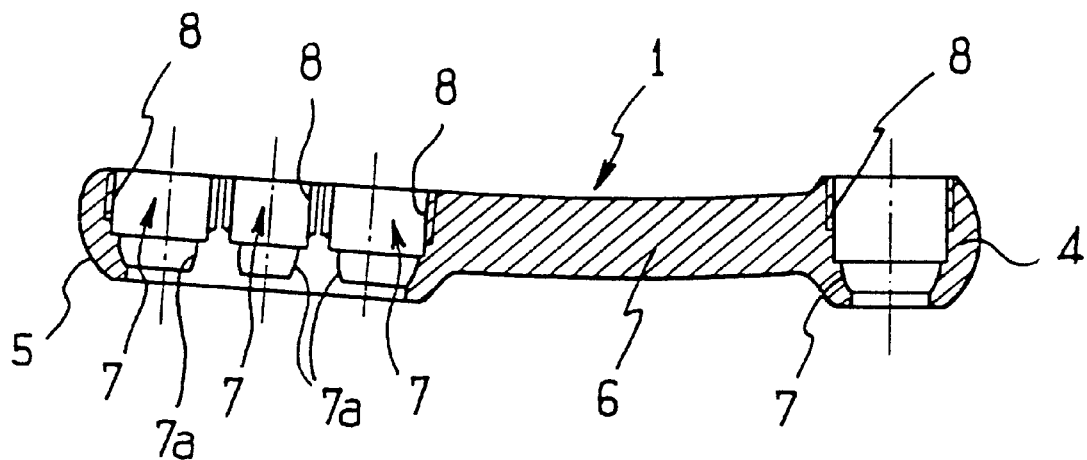
FIG_1
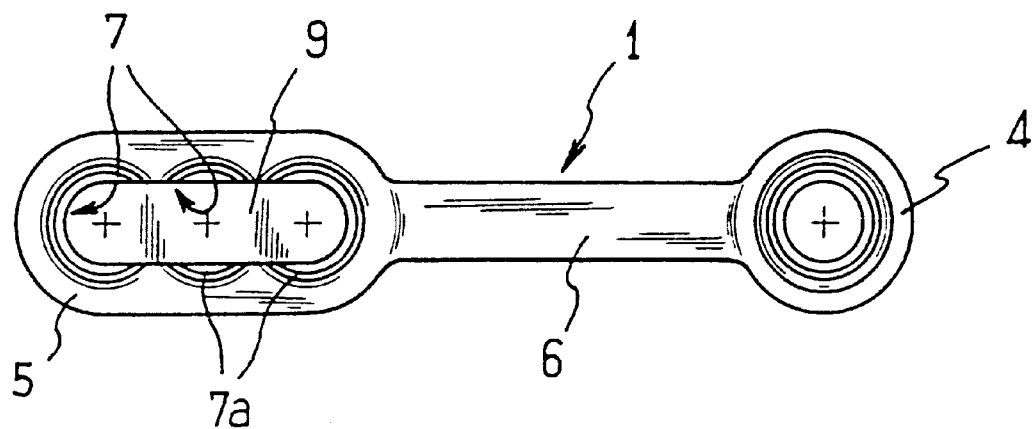
FIG_2

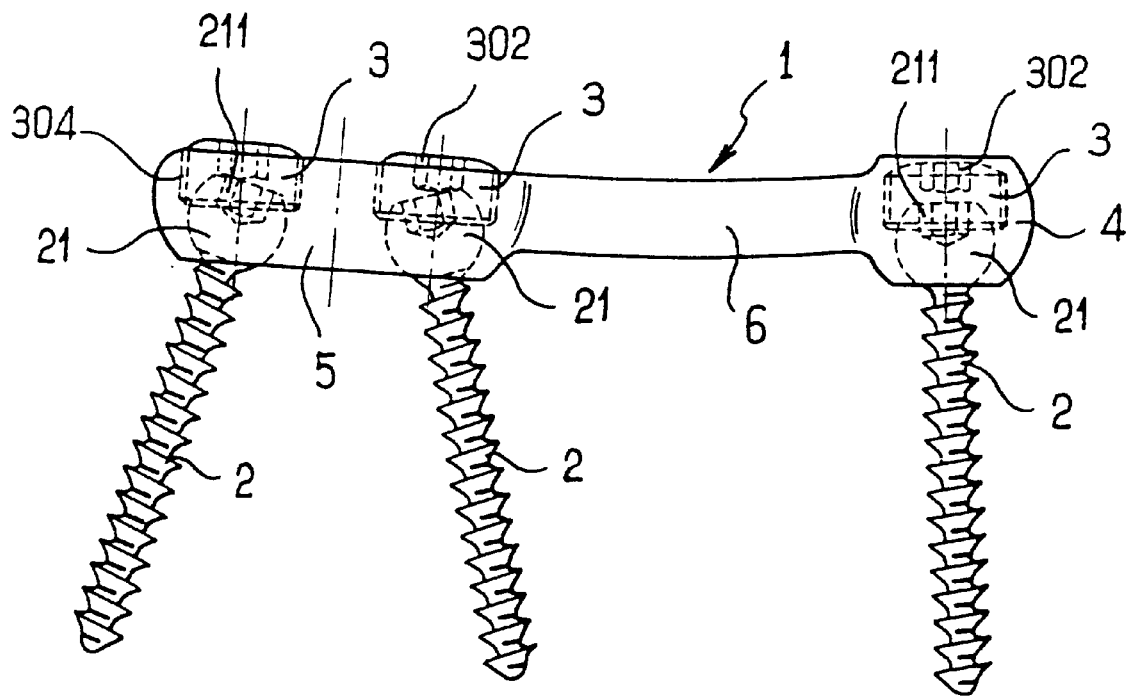
FIG_3
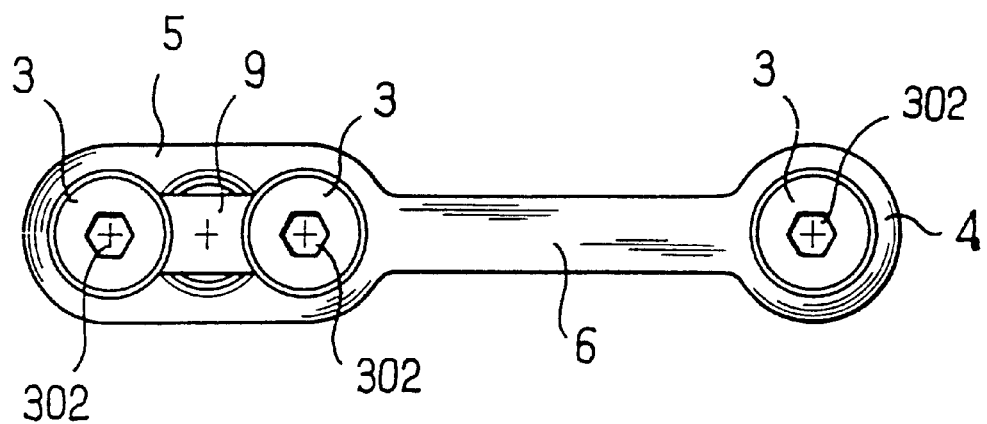
FIG_4

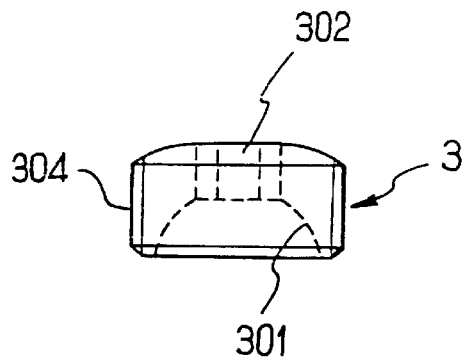
FIG_5
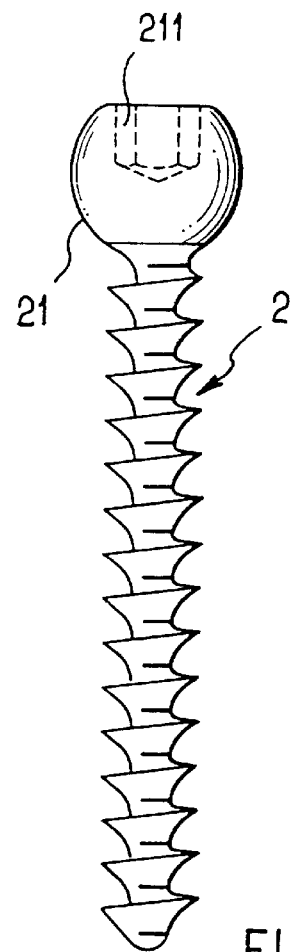
FIG_6
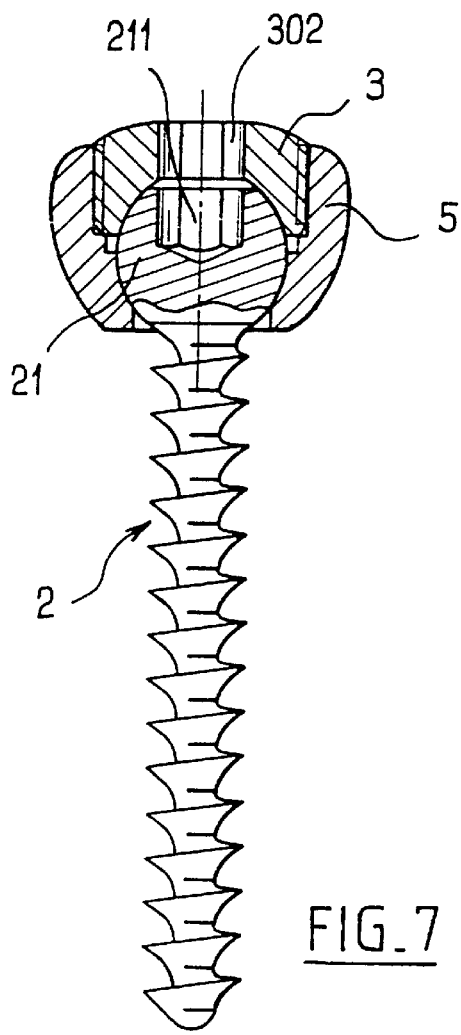
FIG_7

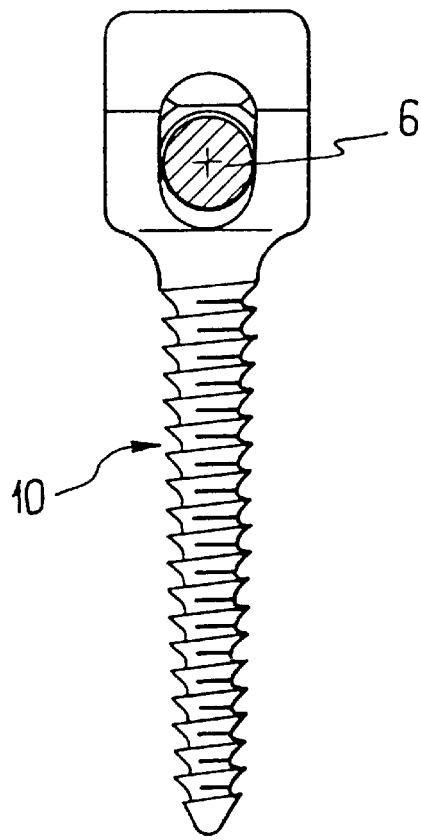
FIG_8
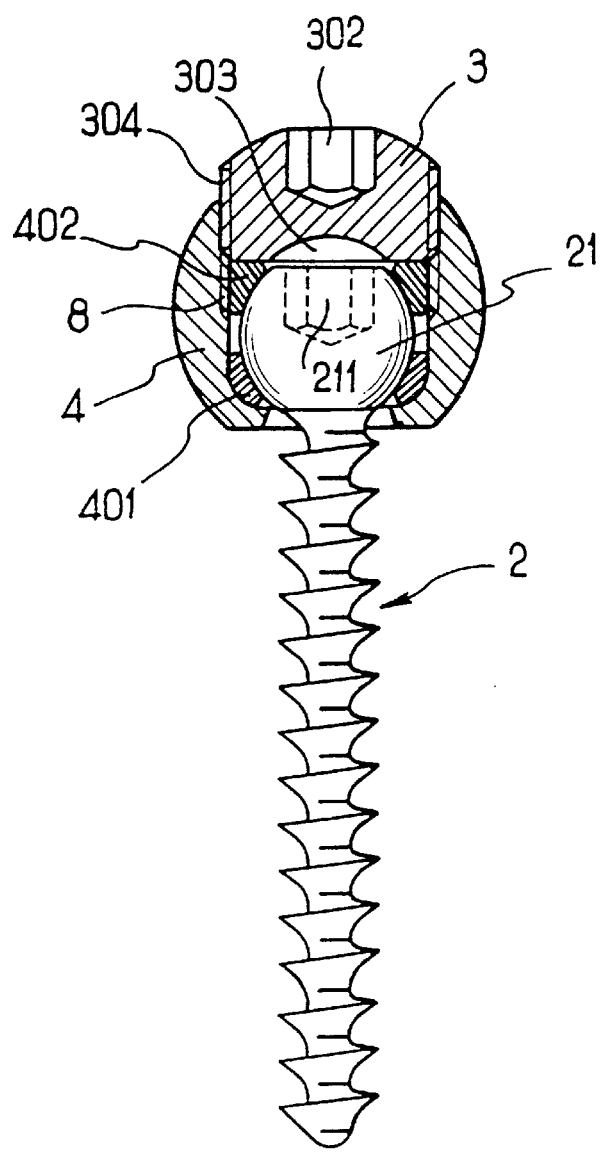
FIG_9

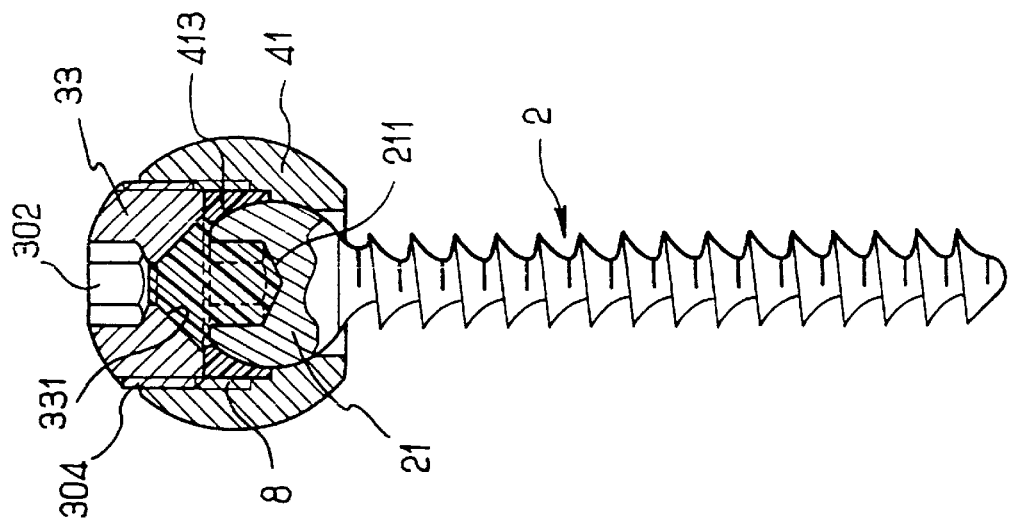
FIG_12
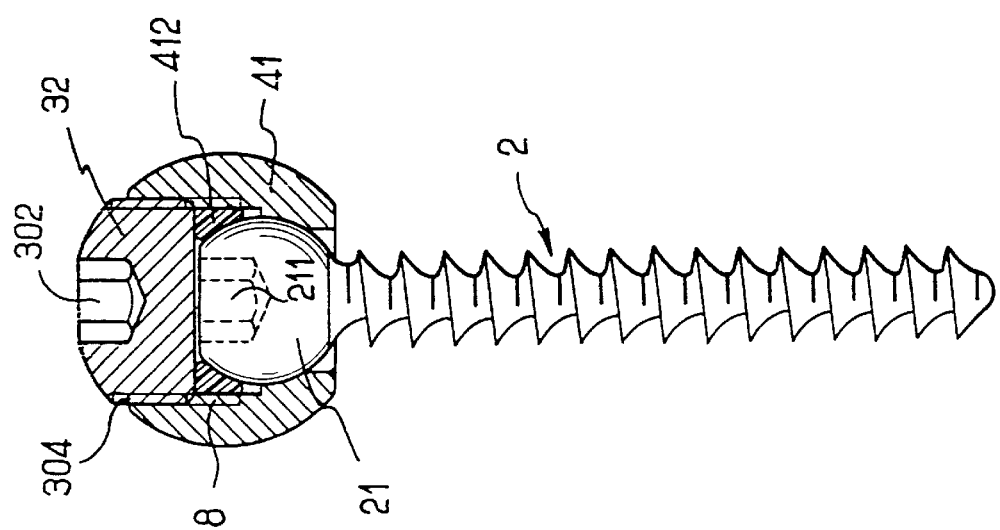
FIG_11
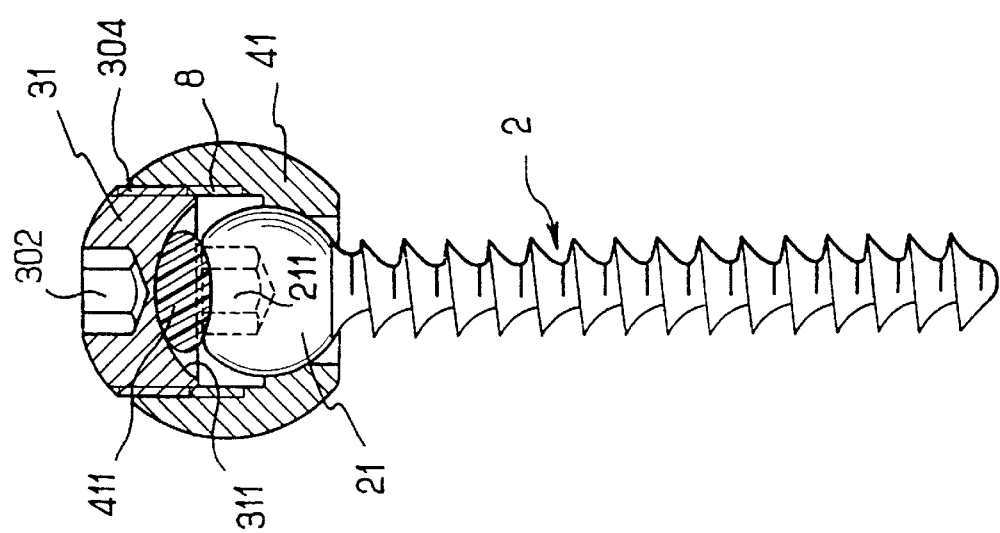
FIG_10

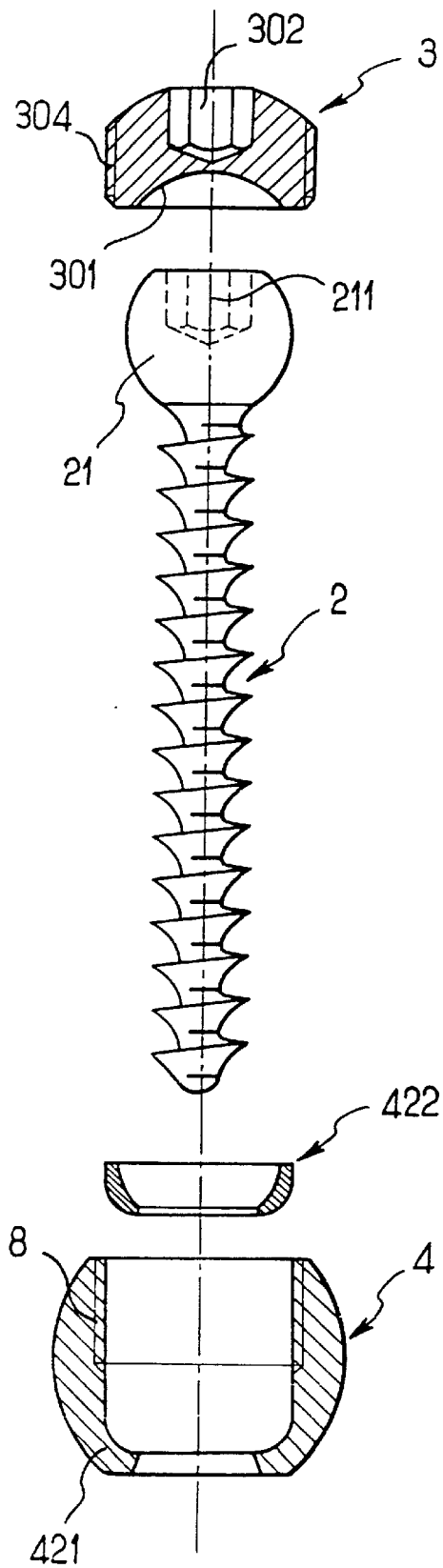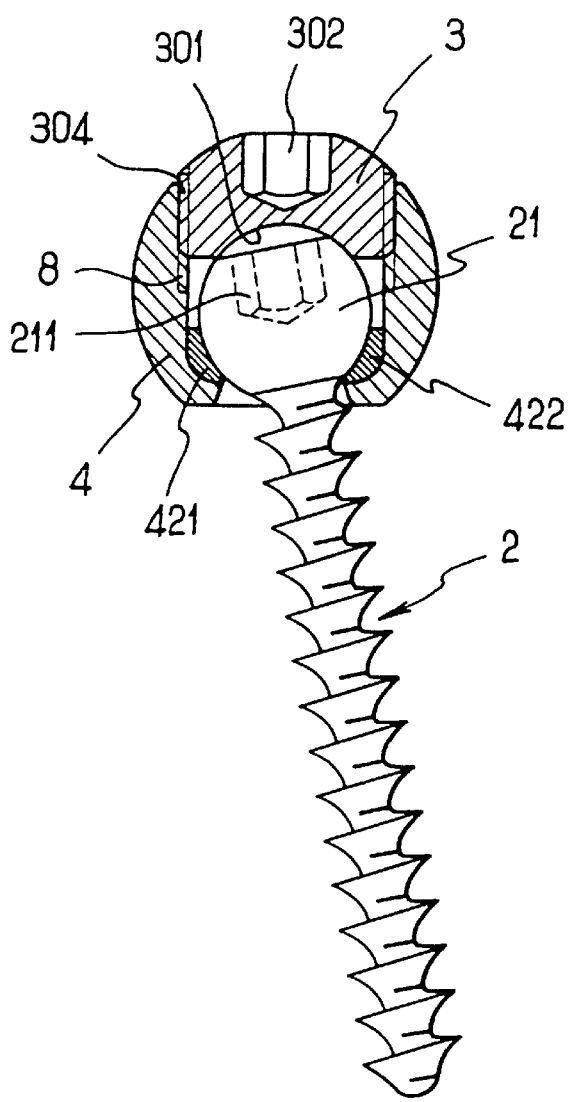
FIG. 13
FIG. 14

BONE FIXING DEVICE, IN PARTICULAR FOR FIXING TO THE SACRUM DURING OSTEOSYNTHESIS OF THE BACKBONE

The present invention relates in general to a fixing device, in particular for fixing to the sacrum and usable during osteosynthesis of the backbone.

BACKGROUND OF THE INVENTION

It is commonplace to perform osteosynthesis of the backbone by using fixing devices that are fastened to the sacrum. This makes it possible to perform reduction movements between the various fixed stages, which movements can be contractions, distractions, or indeed reversals of vertebrae that have slipped forwards relative to the backbone, where the latter condition is known as "spondylolisthesis".

Distraction is often performed for reduction of spondylolisthesis. Partial reduction is thus obtained by putting the fibers of the patient's ligament and disk apparatus back under tension. Reduction is completed by using equipment in accordance with the operating technique associated therewith. Except under exceptional circumstances, the operation is performed bilaterally. Throughout the description below, only one side of the treatment is described.

Most blocks or plates known in the prior art for fixing to the sacrum suffer from certain drawbacks. One of these drawbacks lies in that the orientation of the bone-fastening screws is fixed, which means that the device clearly lacks flexibility in use, given variations from one patient to another concerning the configuration of the sacrum and the neighborhood thereof.

Another drawback of known plates or blocks for fixing to the sacrum lies in the risk of the fastening screws becoming unscrewed, particularly under the effect of relative micro-movements that occur between the equipment and the sacrum. This can result in failure of the fixing to the sacrum.

Also, backbone osteosynthesis can be performed by using equipment serving to fix various functional units of the spinal column, often in a very rigid manner. This gives rise to a sudden change in the distribution of forces, and thus to resulting stress and deformation states for the disks underlying and overlying the fixing. At some stage in the long term, this modification gives rise to degeneration of the disks. This condition is known as the "hinge syndrome".

Document EP-A-0 625 337 discloses a bone fixing device, in particular for fixing the sacrum for osteosynthesis of the backbone, the device comprising elongate link means receiving at least one bone-fastening screw, which screw passes through an orifice formed in the link means, in which the link means include in the bottom region thereof a bearing surface of essentially circular cross-section, in which the head of the screw has a surface that is essentially spherical for bearing against said bearing surface, and in which the link means include a first thread in the orifice, the device also including a plug having a second thread suitable for co-operating with the first thread and for coming into clamping contact with said screw head to hold it in a desired angular position. That device enables the inclination of the screws relative to an elongate link element to be varied, and it also enables the spacing between the screws to be varied.

Nevertheless, that known device is disadvantageous in that the elongate link means are constituted by a plurality of components, specifically an elongate member of cup-shape and a plurality of fixing blocks distributed along the elongate member, each receiving the head of a screw, and at the bottom, a zone corresponding to the elongate member. This means that it is extremely fiddly for the surgeon to handle the device and put it into place, and in particular it is necessary to slide a series of fixing blocks along the elongate member, and to hold them in position thereon.

OBJECTS AND SUMMARY OF THE INVENTION

A first object of the present invention is to mitigate that drawback.

To this end, the invention provides a bone fixing device of the type defined above, wherein the link means are constituted by a single-piece plate-shaped element having the orifice and the first thread formed therein, and wherein said bearing surface is essentially spherical.

Preferred, but non-limiting aspects of the device of the invention are the following:

the first thread is a tapping formed internally in the orifice at a distance from said bottom, and the plug has an outside thread;

the screw head also has a generally spherical top, and the plug has a complementary internal spherical cavity;

said plate includes a series of orifices in alignment that are interconnected by a slot enabling a bone-fastening screw to be moved from one orifice to another before tightening;

said screw head and said plug have identical tightening sockets;

said plate is designed to be fixed to a first bone and forms an integral portion of an element that also includes an eyelet for another bone-fastening screw for fastening to a second bone, together with a rod interconnecting said plate and said eyelet;

the device further includes a bone-fastening device for fastening to another bone, to which said rod is fixed;

the device includes at least two bone-fastening screws passing through respective orifices formed in said plate, and the two screws are suitable for taking up two different angular positions;

the device further includes means for attenuating the stiffness of the assembly between at least one of the bone-fastening screws and said element;

said means for attenuating stiffness comprise at least one piece of flexible material interposed and compressed between said screw head and the associated plug;

the device is associated with a plurality of pieces of flexible material having different flexibilities, thereby enabling different degrees of stiffness attenuation to be provided without requiring action to be taken on the torque with which the plug is tightened;

said piece is an O-ring;

said piece is a pellet;

said stiffness attenuation means comprise a thixotropic fluid interposed between and compressed between the plug and said screw head;

said spherical bearing surface of said orifice is formed by deforming an O-ring placed in a bottom region of said orifice;

said spherical bearing surface of said orifice is constituted by a surface of a rigid ring fitted in a bottom region of said orifice;

said rigid ring is made of a material selected from the group comprising: ceramic-coated titanium alloys, titanium alloys treated by ion bombardment, and solid ceramics;

the stiffness attenuation means further include a surface coating suitable for reducing friction between said essentially spherical bearing surface and said complementary surface of the screw head; and said surface coating is made by nitrogen ion bombardment.

BRIEF DESCRIPTION OF THE DRAWINGS

Other aspects, objects, and advantages of the present invention appear more clearly on reading the following detailed description of preferred embodiments thereof given by way of example and made with reference to the accompanying drawings, in which:

FIG. 1 is a mid longitudinal section view through a fixing element of the invention;

FIG. 2 is a front view of the FIG. 1 element;

FIG. 3 is a side view of the element together with three bone-fastening screws and the associated plugs;

FIG. 4 is a front view of the element provided with screws and plugs;

FIG. 5 is a side view in elevation of a plug for co-operating with the screw of FIG. 6 and the element of FIGS. 1 and 2;

FIG. 6 is a side view in elevation of a bone-fastening screw for co-operating with the element of FIGS. 1 and 2;

FIG. 7 is a cross-section view of the fixing element, a bone-fastening screw, and the associated plug, after assembly;

FIG. 8 is a view partially in elevation and partially in section through an auxiliary bone-fastening screw designed to co-operate with another portion of the fixing element of FIGS. 1 and 2;

FIGS. 9 to 12 are cross-section views analogous to FIG. 4, through four variant embodiments of the invention;

FIG. 13 is a cross-section view through the various components of a fifth variant embodiment of the invention; and FIG. 14 is a cross-section view through the fifth variant in the assembled state.

MORE DETAILED DESCRIPTION

As a preliminary point, it should be observed that elements or portions that are identical or similar from one figure to another are designated, wherever possible, by the same reference symbols, and are not described again on each occasion.

With reference now to FIGS. 1 and 2, there can be seen a sacrum-fixing element given overall reference 1 and made up of three portions: an upper eyelet 4, a sacrum plate 5, and a rod 6, e.g. a cylindrical rod, interconnection the eyelet and the plate. In profile, the overall shape of the element 1 is curved to comply with lordosis, as can be seen in FIG. 1.

A series of holes 7 is formed through the plate 5 in alignment with the long direction of the element 1 and for receiving bone-fastening screws 2.

Preferably, a range of models for the element 1 is offered to the surgeon, different models having, in particular, different lengths of rod 6, and within the plate 5, different numbers of holes for bone-fastening screws.

As shown in FIG. 3, in a three-hole version, the plate 5 may receive two bone-fastening screws 2, while in a five-hole version (not shown), it may receive three bone-fastening screws 2.

The holes 7 are in communication with one another via an oblong section through slot 9 as can be seen in FIG. 2. This slot makes it easy to pass a screw 2 from one position to another while performing reduction. In the region of its bottom, each of these holes includes a spherical cup 7a for co-operating with a complementary bottom portion of the head 21 of the screw 2, said head 21 being generally spherical in shape and having a tightening socket 211, e.g. of the hexagonal type.

This shape for each hole 7 and for the associated screw head 21 allows each screw to move within a solid angle where the half-angle at the apex is, for example, of the order of 30°.

In addition, since each screw is stabilized in its housing while it is being installed, two screws that are distant from each other are suitable for maintaining bone distraction without requiring the use of a distractor instrument.

As shown in particular in FIGS. 1 and 7, each hole 7 possesses internally, at a distance from the cup 7a, a thread in the form of a tapping 8 which enables it to receive a plug 3, shown in detail in FIG. 5. The outside face of the plug includes a tightening socket 302 which is preferably identical to that in the screw head 21 so that the same tightening tool can be used, and a spherical cup-shaped housing 301 co-operating with the similarly spherical top of the screw head 21. The periphery of the plug is threaded at 304 in order to co-operate with the tapping 8 in the hole 7. The purpose of the plug 3, after being screwed into place and tightened, is to lock the screw 2 in an angular position as determined by the surgeon.

The plate 5, the screw 2, and the plug 3, once assembled together, are shown in FIG. 7. The threaded plug 3 performs a non-return function preventing any accidental unscrewing of the associated bone-fastening screw 2, particularly under the conditions explained in the preamble of the present application.

Also, by means of the device of the present invention, spondylolisthesis can be reduced by implanting in the pedicle of the vertebra concerned either an intermediate screw fixed on the intermediate link rod 6, or a screw placed in the eyelet 4.

In the first case, the intermediate rod 6 can thus be used to reverse the vertebra. To this end, and as shown in FIG. 8, it can be associated with a top-loading screw, given overall reference 10 and known per se, and which is previously implanted in the vertebra in question.

It is also possible to secure the vertebra that is to be moved to the intermediate rod 6 by means of a different type of device that is not shown, but that is likewise known per se, in which the screw is offset relative to the axis of the rod 6 but is connected thereto by a holding system.

In the second case, it is the top eyelet 4 of the element 1 which is used to receive the bone-fastening screw 2 engaged in the vertebra that is to be treated, said screw 2 being preferably of the same type as described above. To this end, a hole 7 identical to that described with reference to the plate 5, is formed through said eyelet, so as to allow the screw 2 to be moved angularly and so as to provide a non-return function by means of a plug 3, thus preventing the screw becoming loose.

In order to avoid giving rise to the hinge syndrome as described in the preamble, it is possible to avoid locking firmly the screw 2 that is inserted through the top eyelet 4. Under such circumstances, the screw 2 retains a certain amount of mobility relative to the eyelet 4.

In this way, the position of the vertebra in which the screw 2 inserted through the eyelet 4 is engaged is indeed fixed, but the underlying intervertebral disk continues to function, to some extent. A rigidity gradient is thus established in the fixing which has the effect of attenuating the sudden change of stress state at the overlying disk.

This relative mobility between the screw 2 and the eyelet 4 can be provided in various ways.

A first technique, not shown, consists in using the same principle as that shown in FIG. 7, i.e. using a threaded plug 3 and providing a shoulder in the hole 7 in the eyelet that prevents the plug 3 from reaching a position in which it locks the angular position of the screw 2.

In a variant, also not shown, such a shoulder may be formed on the threaded plug 3.

Also, or alternatively, it is possible to reduce friction between the plug 3 and the head 21 of the screw 2 to a negligible quantity by applying a thin layer of a low coefficient of friction coating, e.g. of ceramic type or of diamond like carbon, on one or more of the various surfaces in contact, i.e. the head of the screw 21, the cup 7a of the hole 7 in the eyelet 4, and the cup 301 in the threaded plug 3.

For example, such a coating may be applied solely to the head 21 of the screw 2.

With reference now to FIGS. 9 to 14, several variant embodiments are described that serve to attenuate the stiffness of the assembly between the screw 2 and the eyelet in which it is engaged, likewise for the purpose of avoiding the hinge syndrome.

Thus, FIG. 9 shows a technique in which all contact is avoided between the rigid parts that need to move relative to one another by using a bottom, first O-ring 401 and a top, second O-ring 402. These two rings are preferably made of a damping material such as silicone, and they are shown in FIG. 9 in the deformed state after the plug has been tightened.

Thus, when the rings 401 and 402 are compressed and deformed during tightening, they provide a connection of attenuated stiffness between the screw 2 and the eyelet 4.

Advantageously, rings having different hardness characteristics but all having the same dimensions, are made available to the surgeon, thereby enabling the surgeon to vary the stiffness of the assembly without having to adapt the extent to which the threaded plug 3 is tightened, since that can be very difficult to implement in reliable manner.

Also, in order to minimize friction between the rings 401 & 402 and the head 21 of the screw, it may be advantageous to apply surface treatment to the screw by nitrogen ion bombardment, thereby improving the tribological characteristic of the head of the screw.

Still with reference to FIG. 9, it can be seen that in this case the plug 3 continues to have a spherical cup 303 that is intended solely to enable the angle of the screw 2 to be varied but without applying locking thrust against the head 21 of said screw.

FIG. 10 shows a variant in which the plug 31 differs from that of FIG. 5 in that its cup, referenced 311 is no longer complementary to the spherical head 21 of the screw 2, but is more flared, so that a pellet 411 of damping material can be interposed between the cup 311 and said head 21, and can be compressed and deformed when tightening the plug.

This also provides attenuation of the overall stiffness of the assembly.

FIG. 11 shows a variant in which the threaded plug 32 has a plane working surface and in which direct contact between the plug 32 and the head of the screw 21 is avoided by using an O-ring 412 made of a damping material, which is compressed and deformed when the plug is tightened.

FIG. 12 shows a variant in which the plug, given reference 33, has a conical recess 331 in its working face, and in which contact between the plug 33 and the screw head 21 is avoided by injecting a thixotropic fluid 412 while the appliance is being installed, thereby likewise performing the damping function.

In addition, in the three variant embodiments of FIGS. 10, 11, and 12, contact friction between the spherical head 21 and the cup 7a of the hole 7 formed in the eyelet 4 can also be reduced by using a coating of the kind mentioned above. In this respect, the coating used in the variant of FIG. 12 should be selected so that contact between the base of the spherical head 21 and the cup 7a seals the thixotropic fluid even when compressed by tightening the plug.

FIGS. 13 and 14 show another variant embodiment in which the eyelet is modified. More precisely, the eyelet 4 has a generally cylindrical cup 421 in which the portion remote from the bottom is tapped at 8 to receive the threaded plug 3, identical to that of FIG. 5.

A ring 422 is interposed between the cup 421 and the screw head 21. It may either be a rigid ring, e.g. made of a ceramic-coated titanium alloy, or of titanium alloy treated by ion bombardment, or indeed of solid ceramic, or else it may be an O-ring identical to the ring 401 used in the variant embodiment of FIG. 9, likewise made of a damping material, e.g. silicone.

When the ring 422 is rigid, it may be advantageous for the radius of curvature of its internal spherical bearing surface to have a value that is slightly smaller than the radius of the screw head 21, so as to ensure that said screw head is stressed on tightening. In which case the version of FIGS. 13 and 14 can advantageously also be used when it is desired to lock the screw fully.

In another variant, the ring 422 can be split, there again with the head 21 being put under stress and with the option of locking.

Naturally, the parts such as the element 1, the screws 2, and the plugs 3 are all made of biocompatible materials having appropriate mechanical properties, e.g. a titanium alloy.

Various additional remarks are given below to finish off.

Firstly, the shape and the dimensions of the element 1 are selected so as to enable it to withstand twisting stresses, by means of the plane bearing surface generated between the base of the plate-shaped portion 5 and the adjacent bone.

This shape also makes it possible to limit movement in longitudinal translation on the intermediate screws.

Thereafter, the above-described means for attenuating stiffness provide such attenuation both in the sagittal plane and in the transverse plane.

Finally, the invention makes it possible to offer an osteosynthesis system that is highly modular: thus, for example, different versions of the ring 422 can be offered to the practitioner for adjusting the anterior contact zone (adjacent to the vertebra), whereas one of the above-described damping means can be offered with various different degrees of stiffness so as to adapt damping in the posterior portion (adjacent to the plug). In practice, this makes it possible to cover the entire range between flexible links and rigid links.

In this respect, it will be observed that the above-described stiffness-attenuating means can be used both with the screw in the eyelet 4 and with the screws in the plate 5.

Naturally, the present invention is not limited in any way to the various embodiments described and shown, and the person skilled in the art will be able to make variations or modifications within the spirit of the invention.

I claim:

1. A bone fixing device for fixing the sacrum to an adjacent vertebra during osteosynthesis of the backbone, the device comprising:

a plurality of bone fastening screws, each screw having a head wherein at least one of the plurality of bone fastening screws is a top-loading screw;

an elongated member having a first portion and second portion coupled between a cylindrical rod having a cylindrical circumference, each portion and the cylindrical rod being in general alignment relative to one another, the elongated member further having a means for receiving at least two bone-fastening screws at an angle in the first portion and for receiving at least one bone fastening screw at an angle in the second portion, the heads of each bone fastening screw being in general alignment relative to one another;

wherein the top-loading screw is fixed about the cylindrical circumference of the cylindrical rod; and a means for securing each bone fastening screw to the elongated member at an angle.

2. The device of claim 1, the head of each screw having a bottom portion, the bottom portion having a spherical profile, each means for receiving comprising an orifice through which a bone fastening screw may pass, the orifice further defined by a bottom region and a top region, the bottom region having a spherical profile complementary to the spherical profile of the screw head so as to act as a bearing surface, the top region having first threads, the means for securing comprising a plug, the plug having second threads adapted to cooperate with the first threads of the top region of the orifice to clamp a bone fastening screw to the elongated member at an angle.

3. The device of claim 2, the head of each screw having a top portion, the top portion having a spherical profile that extends from the bottom portion of the head, the plug further having a concave spherical profile complementary to the spherical profile of the top portion of the screw head.

4. The device of claim 2 wherein each orifice of the first portion is connected by a single longitudinal slot that permits the movement of one bone fastening screw from one bearing surface to another bearing surface without extracting the bone fastening screw from the orifice.

5. A bone fixing device for use in osteosynthesis of the backbone, the device comprising:

an integral link member having a longitudinal direction, a top region having a plurality of first threads, a bottom region, a plurality of spherical bearing surfaces in the bottom region, each spherical bearing surface being adjacent to at least one other spherical bearing surface in the longitudinal direction and associated with one first thread in the top region, the integral link member further having an elongated through orifice coupling each spherical bearing surface;

at least one bone fastening screw adapted to be received in the elongated orifice whereby the bone fastening screw may be moved from one bearing surface to another bearing surface without extracting the screw from the orifice, each screw having a head with an essentially spherical surface adapted to bear against a spherical bearing surface of the integral link member; and at least one plug having a second thread adapted to cooperate with one of the first threads and further adapted to come into clamping contact with the head of at least one bone fastening screw to hold the screw against one of the bearing surfaces in a desired angular position.

6. The device of claim 5 further comprising at least one transition region, wherein each of the bearing surfaces and its associated first threads are mutually truncated at one of the transition regions therebetween.

7. The device of claim 5, the elongated through orifice having an end and a major axis having a direction, the integral link member further having a linking portion, the linking portion adapted to extend from one end of the elongated through orifice in a direction corresponding to the major axis of the elongated through orifice.

8. The device of claim 5, the head of each screw further having a top portion of an essentially spherical shape, the plug further having a bottom surface, the bottom surface having a spherical cavity that is complementary in shape to the spherical shape of the top portion of each screw head.

9. The device of claim 5 wherein the elongated through orifice has a length adapted to simultaneously receive at least two bone fastening screws and at least two corresponding plugs.

10. A bone fixing device for use in osteosynthesis of the backbone, the device comprising:

a link member having a through orifice, the through orifice having a top region having a first thread and a bottom region having a spherical bearing surface;

a bone fastening screw adapted to be received in the orifice, the bone fastening screw having a head with an essentially spherical surface adapted to bear against the spherical bearing surface;

a plug having a second thread adapted to cooperate with the first thread and further adapted to come into clamping contact with the head of the bone fastening screw through torque applied to the plug to hold the screw against the bearing surface in a desired angular position, thus creating a stiffness of assembly; and a stiffness-attenuating material coupled to at least part of the screw head whereby stiffness of assembly between the link member and the bone fastening screw is reduced.

11. The device of claim 10 wherein the stiffness-attenuating material comprises at least one piece of flexible material interposed and compressed between the screw head and the plug.

12. The device of claim 11 wherein the stiffness-attenuating material is comprised of a plurality of flexible materials, each flexible material having different flexibilities so as to enable different degrees of stiffness attenuation between the link member and the bone fastening screw without varying the torque applied to the plug from one flexible material to another flexible material.

13. The device of claim 11 wherein the one piece of flexible material is an O-ring.

14. The device of claim 11 wherein the one piece of flexible material is a pellet.

15. The device of claim 10 wherein the stiffness-attenuating material comprises a thixotropic fluid interposed and compressed between the plug and the screw head.

16. The device of claim 10 wherein the stiffness-attenuating material comprises a surface coating suitable for reducing friction between the essentially spherical bearing surface and the complementary surface of the screw head.

17. The device of claim 16 wherein the surface coating is made by nitrogen ion bombardment.

18. A bone fixing device for use in osteosynthesis of the backbone, the device comprising:

a link member having a through orifice, the through orifice having a top region having a first thread and a bottom region;

a flexible O-ring in the shape of spherical bearing surface and located in the bottom region of the orifice;

a bone fastening screw adapted to be received in the orifice, the bone fastening screw having a head with an essentially spherical surface adapted to bear against the spherical bearing surface; and a plug having a second thread adapted to cooperate with the first thread and further adapted to come into clamping contact with the head of the bone fastening screw through torque applied to the plug to hold the screw against the bearing surface in a desired angular position, thus creating a stiffness of assembly.

19. A bone fixing device for use in osteosynthesis of the backbone, the device comprising:

a link member having a through orifice, the through orifice having a top region having a first thread and a bottom region;

a cylindrical rod having a cylindrical circumference;

a rigid ring in the shape of spherical bearing surface and located in the bottom region of the orifice;

a bone fastening screw adapted to be received in the orifice, the bone fastening screw having a head with an essentially spherical surface adapted to bear against the spherical bearing surface;

a top-loading screw fixed about the cylindrical circumference of the cylindrical rod; and a plug having a second thread adapted to cooperate with the first thread and further adapted to come into clamping contact with the head of the bone fastening screw through torque applied to the plug to hold the screw against the bearing surface in a desired angular position, thus creating a stiffness of assembly.

20. The device of claim 19 wherein the rigid ring is made of a material selected from the group comprising: ceramic-coated titanium alloys, titanium alloys treated by ion bombardment, and solid ceramics.

* * * * *